US00PP14864P2

(12) United States Plant Patent
Hofmann

(10) Patent No.: US PP14,864 P2
(45) Date of Patent: Jun. 8, 2004

(54) NEW GUINEA IMPATIENS PLANT NAMED 'FISNICS HOT ROSE'

(50) Latin Name: *Impatiens hawkeri*
Varietal Denomination: Fisnics Hot Rose

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/453,126

(22) Filed: Jun. 3, 2003

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisnics Hot Rose', characterized by its outwardly spreading and uniformly mounded plant habit; medium growth habit; freely branching and freely flowering habit; dark green-colored foliage, occasionally variegated; and large, slightly oblong, red purple-colored flowers that are positioned above and beyond the foliage.

1 Drawing Sheet

Botanical classification/cultivar designation: *Impatiens hawkeri* cultivar Fisnics Hot Rose.

BACKGROUND OF THE INVENTION

The present Invention relates to a new and distinct cultivar of New Guinea Impatiens plant, botanically known as *Impatiens hawkeri*, and hereinafter referred to by the name 'Fisnics Hot Rose'.

The new Impatiens is a product of a planned breeding program conducted by the Inventor in Hillscheid, Germany and Galder, Gran Canaria, Spain. The objective of the breeding program is to develop new medium-sized Impatiens cultivars with an early to medium flowering response and large rounded flowers with attractive coloration.

The new Impatiens originated from a cross-pollination made by the Inventor during the spring of 1999 of the *Impatiens hawkeri* cultivar Fisimp 171, disclosed in U.S. Plant Pat. No. 13,703, as the female, or seed, parent with a proprietary seedling selection of *Impatiens hawkeri* identified as code number K98-4173-9, not patented, as the male, or pollen, parent. The cultivar Fisnics Hot Rose was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisnics Hot Rose'. These characteristics in combination distinguish 'Fisnics Hot Rose' as a new and distinct Impatiens cultivar:

1. Outwardly spreading and uniformly mounded plant habit; medium growth habit.
2. Freely branching and freely flowering habit.
3. Dark green-colored foliage, occasionally variegated.

4. Large, slightly oblong, red purple-colored flowers that are positioned above and beyond the foliage.

Plants of the new Impatiens can be compared to plants of the female parent, the cultivar Fisimp 171. In side-by-side comparisons conducted by the Inventor in Hillscheid, Germany, plants of the new Impatiens differed from plants of the Fisimp 171 in the following characteristics:

1. Plants of the new Impatiens occasionally had variegated foliage whereas plants of the Fisimp 171 did not have variegated foliage.
2. Flowers of plants of the new Impatiens were more blue and not as red in color than flowers of plants of the Fisimp 171.

Plants of the new Impatiens can be compared to plants of the male parent selection. In side-by-side comparisons conducted by the Inventor in Hillscheid, Germany, plants of the new Impatiens differed from plants of the male parent selection in the following characteristics:

1. Plants of the new Impatiens and the male parent selection differed in leaf and leaf venation coloration.
2. Plants of the new Impatiens and the male parent selection differed in flower coloration.

Plants of the new Impatiens can also be compared to plants of the cultivar Balcebpurp, disclosed in U.S. Plant Pat. No. 13,999. In side-by-side comparisons conducted by the Inventor in Hillscheid, Germany, plants of the new Impatiens differed from plants of the cultivar Balcebpurp in the following characteristics:

1. Plants of the new Impatiens were taller than plants of the cultivar Balcebpurp.
2. When variegation was present, leaves of plants of the new Impatiens were more distinctly variegated than leaves of plants of the cultivar Balcebpurp.
3. Plants of the new Impatiens had larger flowers than plants of the cultivar Balcebpurp.
4. Flowers of plants of the new Impatiens and the cultivar Balcebpurp differed slightly in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisnics Hot Rose' grown in a container.

DETAILED BOTANICAL DESCRIPTION

The cultivar Fisnics Hot Rose has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics Hot Rose.

Parentage:

*Female parent.*—*Impatiens hawkeri* cultivar Fisimp 171, disclosed in U.S. Plant Pat. No. 13,703.

*Male parent.*—Proprietary seedling selection of *Impatiens hawkeri* identified as code number K98-4173-9, not patented.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D in color.

Plant description:

*General appearance.*—Outwardly spreading and uniformly mounded plant growth habit; medium growth habit; freely branching habit; bushy appearance; freely flowering. Moderately vigorous.

*Crop time.*—From a rooted cutting, about 9 to 10 weeks are required to produce finished flowering plants in 12-cm containers.

*Plant height.*—About 19.5 cm.

*Plant diameter or spread.*—About 38 to 43 cm.

*Lateral branches.*—Quantity per plant: About 8. Length: About 15 to 17 cm. Diameter: About 7 to 8 mm. Internode length: About 4.5 to 5.5 cm. Texture: Smooth, glabrous. Color: 145A; towards the nodes, 181A.

*Foliage description.*—Arrangement: Primarily in whorls. Length: About 14.5 to 15.5 cm. Width: About 4.5 to 4.8 cm. Shape: Elliptic; narrow. Apex: Acuminate. Base: Acute. Margin: Serrulate with ciliation. Texture: Smooth, slightly rugose; glabrous. Color: Developing foliage, upper surface: 137B. Developing foliage, lower surface: 138B. Fully expanded foliage, upper surface: Between 137A and 139A; occasionally variegated, central stripe, 154A to 6A. Fully expanded foliage, lower surface: 138B. Venation, upper surface: 47D. Venation, lower surface: 145C. Petiole: Length: About 1 to 1.5 cm. Diameter: About 3 mm. Texture: Smooth, glabrous. Color, upper surface: 47C. Color, lower surface: 145C.

Flower description:

*Flower type and flowering habit.*—Single, large, slightly oblong, and red purple-colored flowers. Freely and continuously flowering; usually about 6 to 8 flowers and flower buds per lateral branch. Flowers positioned above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 weeks after planting.

*Flower buds.*—Length: About 2.4 cm. Diameter: About 1.4 to 1.5 cm. Shape: Ovoid. Color: 58B.

*Flower length.*—About 7.3 to 7.5 cm.

*Flower width.*—About 6.5 to 7 cm.

*Flower depth.*—About 1 cm.

*Petals.*—Quantity: Five per flower, imbricate. Length: Banner petals: About 3 to 3.3 cm. Lateral and base petals: About 3 to 3.5 cm. Width: Banner petal: About 4.5 to 4.8 cm. Lateral and base petals: About 3 to 4 cm. Shape: Cordate. Apex: Distinctly lobed; emarginate. Base: Attenuate. Margin: Entire. Aspect: Mostly flat. Texture: Smooth; satiny. Color: When opening, upper surface: 57B. When opening, lower surface: 58B. Fully opened, upper surface: 57C; fine central longitudinal stripe, 46B; color becoming closer to 57D with development. Fully opened, lower surface: 58B to 58C.

*Spur.*—Quantity: One per flower. Length: About 5.5 to 5.8 cm. Diameter: At apex: About 0.5 mm. At flower: About 3 mm. Aspect: Curved. Color: 53D.

*Peduncles.*—Length: About 5 to 5.5 cm. Diameter: About 2 mm. Texture: Smooth, glabrous. Strength: Strong, flexible. Color: Towards the stem, 145C; towards the flowers, 179A.

*Reproductive organs.*—Androecium: Stamen number: Five fused at anthers, hooded; filaments free. Anther length: About 5 to 6 mm. Anther shape: Obovate. Anther color: 52A. Pollen amount: Moderate. Pollen color: 8D. Gynoecium: Pistil quantity: One per flower. Pistil length: About 6 mm. Stigma color: 12D. Style color: Close to 12D. Ovary: Five-celled. Ovary color: 143A.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisnics Hot Rose', as illustrated and described.

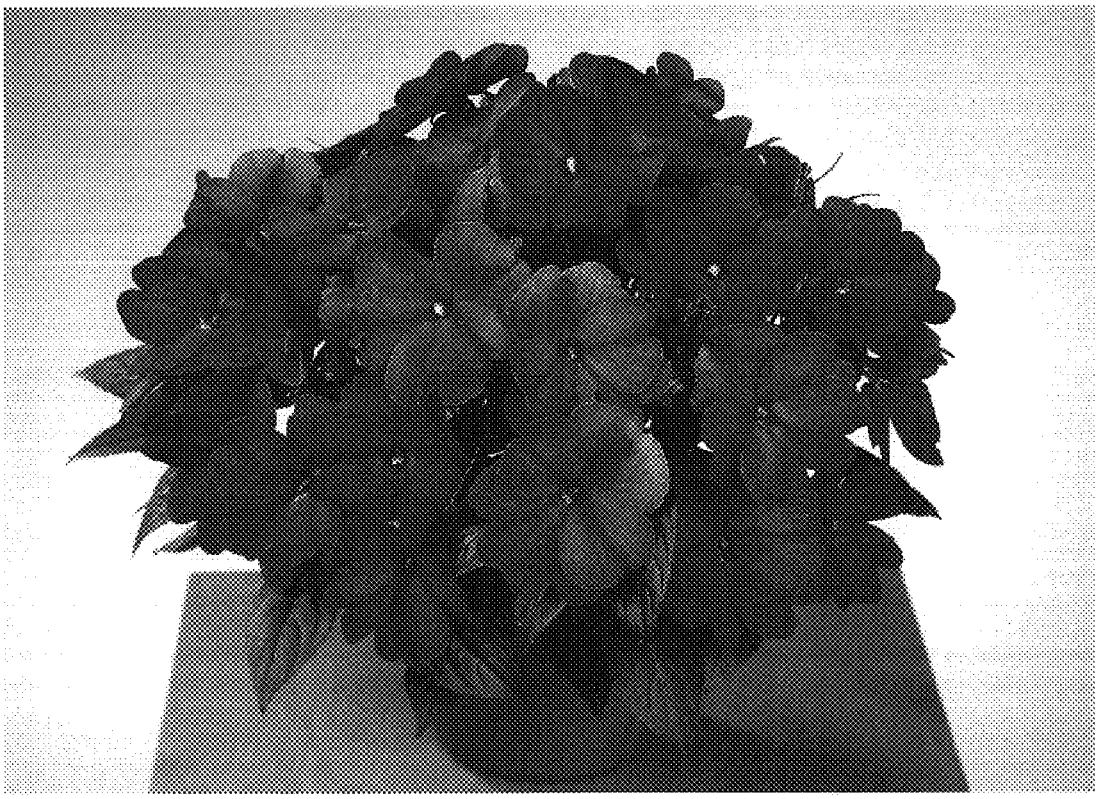

* * * * *